(12) United States Patent
Oh et al.

(10) Patent No.: US 7,553,626 B2
(45) Date of Patent: Jun. 30, 2009

(54) PRIMER SET CAPABLE OF SPECIFICALLY AMPLIFYING A TARGET SEQUENCE FOUND IN 10 BACTERIAL SPECIES AND PROBE OLIGONUCLEOTIDE SPECIFICALLY HYBRIDIZABLE WITH EACH TARGET SEQUENCE OF THE 10 BACTERIAL SPECIES

(75) Inventors: Ji-young Oh, Suwon-si (KR); Nam Huh, Seoul (KR); Sang-hyun Peak, Seoul (KR); Sung-young Jeong, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 11/317,601

(22) Filed: Dec. 23, 2005

(65) Prior Publication Data

US 2006/0246473 A1 Nov. 2, 2006

(30) Foreign Application Priority Data

Dec. 23, 2004 (KR) .................. 10-2004-0111101

(51) Int. Cl.
C12Q 1/68 (2006.01)
C12P 19/34 (2006.01)
C07H 21/04 (2006.01)

(52) U.S. Cl. .................. 435/6; 435/91.2; 536/24.32; 536/24.33

(58) Field of Classification Search .................. None
See application file for complete search history.

(56) References Cited

U.S. PATENT DOCUMENTS

| | | | |
|---|---|---|---|
| 5,445,934 A | 8/1995 | Fodor et al. ............ | 435/6 |
| 5,525,718 A | 6/1996 | Ohashi et al. ............ | 536/24.32 |
| 5,744,305 A | 4/1998 | Fodor et al. ............ | 435/6 |
| 5,830,654 A | 11/1998 | Milliman ............ | 435/6 |
| 6,001,564 A | 12/1999 | Bergeron et al. ............ | 435/6 |
| 6,582,908 B2 * | 6/2003 | Fodor et al. ............ | 435/6 |
| 2003/0175709 A1 * | 9/2003 | Murphy et al. ............ | 435/6 |
| 2004/0072242 A1 * | 4/2004 | Hunter et al. ............ | 435/7.1 |
| 2006/0046246 A1 * | 3/2006 | Zeng et al. ............ | 435/5 |

OTHER PUBLICATIONS

Buck et al. Design strategies and performance of custom DNA sequencing primers. BioTechniques (1999) 27(3): 528-536.*
Rossau et al. DNA probes for *Bordetella* species and a colorimetric reverse hybridization assay for the detection of *Bordetella pertussis*. Molecular and Cellular Probes (1992) 6(4): 281-289.*
GenBank Accession No. U10876 for *Moraxella catarrhalis* 16S rRNA, Jun. 29, 1994 [online], [retrieved on Jun. 7, 2008], retrieved from the Internet: <URL: www.ncbi.nlm.nih.gov/entrez/viewer.fcgi?db=nuccore&id=506691>.*
GenBank Accession No. L06108 for *Chlamydia pneumoniae* 16S rRNA, Sep. 21, 1993 [online], [retrieved on Jun. 7, 2008], retrieved from the Internet: <URL: //www.ncbi.nlm.nih.gov/entrez/viewer.fcgi?db=nuccore&id=174111>.*
GenBank Accession No. X73402 for *Legionella pneumophila* 16S rRNA, Oct. 1, 1993 [online], [retrieved on Jun. 7, 2008], retrieved from the Internet: <URL: www.ncbi.nlm.nih.gov/entrez/viewer.fcgi?db=nuccore&id=405770>.*
GenBank Accession No. M29061 for *Mycoplasma pneumoniae* 16S rRNA, Apr. 27, 1993 [online], [retrieved on Jun. 7, 2008], retrieved from the Internet: <URL: www.ncbi.nlm.nih.gov/entrez/viewer.fcgi?db=nuccore&id=175479>.*
GenBank Accession No. AJ608938 for *Streptococcus pneumoniae* 16S rRNA (May 17, 2004 [online], [retrieved on Jun. 8, 2008], retrieved from the Internet: <URL: http://www.ncbi.nlm.nih.gov/entrez/viewer.fcgi?db=nuccore&id =38520888>.*
Stone et al. Detection of rRNA from four respiratory pathogens using an automated Qβ replicase assay. Molecular and Cellular Probes (1996) 10(5): 359-370.*
Barry, Tom et al.; "A General Method to Generate DNA Probes for Microorganisms"; Bio/Technology; vol. 8; pp. 233-236; 1990.
Jantos, Christian et al.; "Rapid Detection of *Chlamydia pneumoniae* by PCR-Enzyme Immunoassay"; Journal of Clinical Microbiology, pp. 1890-1894; vol. 36, No. 7; Jul. 1998.
Greisen, K. et al.; "PCR Primers and Probes for the 16S rRNA Gene of Most Species of Pathogenic Bacteria, Including Bacteria found in Cerebrospinal Fluid"; Journal of Clinical Microbiology, pp. 335-351; vol. 32(2); Feb. 1994.

(Continued)

*Primary Examiner*—Kenneth R. Horlick
*Assistant Examiner*—Angela Bertagna
(74) *Attorney, Agent, or Firm*—Cantor Colburn LLP (57) ABSTRACT

Provided are a primer set for amplifying a target sequence specific to *Bordetella pertussis, Chlamydophila pneumoniae, Haemophilus influenzae, Klebsiella pneumoniae, Legionella pneumophila, Moraxella catarrhalis, Mycoplasma pneumoniae, Pseudomonas aeruginosa, Stapylococcus aureus*, and *Streptococcus pneumoniae*, the primer set including at least one oligonucleotide of 10 to 100 nucleotides in length, selected from the group consisting of oligonucleotides each of which comprises a fragment of at least 10 contiguous nucleotides present in a sequence as set forth in SEQ ID NO: 1 and at least one oligonucleotides of 10 to 100 nucleotides in length, selected from the group consisting of oligonucleotides each of which comprises a fragment of at least 10 contiguous nucleotides present in a sequence as set forth in SEQ ID NO: 2; and probes specific to a specific species of the 10 bacterial species.

4 Claims, 1 Drawing Sheet

OTHER PUBLICATIONS

Grimm, Dorothee et al.; "Specific Detection of *Legionella pneumophila*: Construction of a New 16S rRNA-Targeted Oligonucleotide Probe"; Appl Environ Microbiol, Jul. 1998, pp. 2686-2690, vol. 64, No. 7.

Ouverney, Cleber et al.; "Combined Microautoradiography-16S rRNA Probe Technique for Determination of Radioisotope Uptake by Specific Microbial Cell Types in Situ"; Appl Environ Microbiol, Apr. 1999, pp. 1746-1752, vol. 65, No. 4.

Yogev, D. et al.; "Distinction of Species and Strains of Mycoplasmas (Mollicutes) by Genomic DNA Fingerprints with an rRNA Gene Probe"; Journal of Clinical Microbiology, Jun. 1998; pp. 1198-1201; vol. 26; No. 6.

Bootsma, Hester et al.; "Analysis of *Moraxella catarrhalis* by DNA Typing: Evidence for a Distinct Subpopulation Associated with Virulence Traits"; Journal of Infectious Diseases; 2000;181: pp. 1376-1387.

* cited by examiner

FIG. 1

PRIMER SET CAPABLE OF SPECIFICALLY AMPLIFYING A TARGET SEQUENCE FOUND IN 10 BACTERIAL SPECIES AND PROBE OLIGONUCLEOTIDE SPECIFICALLY HYBRIDIZABLE WITH EACH TARGET SEQUENCE OF THE 10 BACTERIAL SPECIES

This application claims the priority of Korean Patent Application No. 2004-0111101, filed on Dec. 23, 2004, in the Korean Intellectual Property Office, the disclosure of which is incorporated herein in its entirety by reference.

BACKGROUND OF THE INVENTION

1. Field of the Invention

The present invention relates to a primer set capable of amplifying in common a target sequence found in 10 bacterial species related to respiratory diseases, and to oligonucleotides specific to each target sequence of 10 bacterial species.

2. Description of the Related Art

Numerous conventional probes for detecting viruses related to respiratory diseases have been disclosed. For example, U.S. Pat. No. 5,830,654 discloses hybridization assay probes for *Haemophilus influenzae* which are comprised of an oligonucleotide of 14 to 18 nucleotides. U.S. Pat. No. 5,525,718 discloses oligonucleotides selectively hybridizable with a specific gene (e.g., entE) of *Staphylococcus aureus*. In addition, U.S. Pat. No. 6,001,564 discloses primers or probes specific to each of *Escherichia coli, Klebsiella pneumoniae, Pseudomonas aeruginosa, Proteus mirabilis, Streptococcus pneumoniae, Staphylococcus aureus, Staphylococcus epidermis, Haemophilus influenzae*, and *Moraxella catarrhalis*.

In the conventional example provided above, a primer set capable of amplifying a target sequence common to all 10 bacterial species known to be related to respiratory diseases has not been disclosed. Also, a probe specific for each target sequence of these bacterial species has not been disclosed.

SUMMARY OF THE INVENTION

The present invention provides a primer set capable of amplifying a target sequence found in 10 bacterial species related to respiratory diseases.

The present invention also provides oligonucleotides specific to each target sequence of 10 bacterial species related to respiratory diseases and not cross-hybridizing to nucleic acides of other species.

BRIEF DESCRIPTION OF THE DRAWING

The above and other features and advantages of the present invention will become more apparent by describing in detail exemplary embodiments thereof with reference to the attached drawing in which.

DETAILED DESCRIPTION OF THE INVENTION

The present invention provides a primer set for amplifying a target sequence specific to *Bordetella pertussis, Chlamydophila pneumoniae, Haemophilus influenzae, Klebsiella pneumoniae, Legionella pneumophila, Moraxella catarrhalis, Mycoplasma pneumoniae, Pseudomonas aeruginosa, Stapylococcus aureus*, and *Streptococcus pneumoniae*, comprising at least one oligonucleotide of 10 to 100 nucleotides in length, selected from the group consisting of oligonucleotides each of which comprises a fragment of at least 10 contiguous nucleotides present in a sequence as set forth in SEQ ID NO: 1 and at least one oligonucleotides of 10 to 100 nucleotides in length, selected from the group consisting of oligonucleotides each of which comprises a fragment of at least 10 contiguous nucleotides present in a sequence as set forth in SEQ ID NO: 2.

The primer set of the present invention can be used to amplify a target sequence in the 16S rRNA gene derived from the 10 bacterial species, namely, a polynucleotide comprised of 327 to 529 nucleotides. Since the primer set can amplify the target sequence derived from the 10 bacterial species, the target sequence can be amplified without using a different primer set for each of the bacteria species.

The primer set of the present invention has obtained a sequence common to 119 strains of the 10 bacterial species related to respiratory diseases. The number of stains of each species is as in the following table 1.

TABLE 1

| Species | Number of Strains |
| --- | --- |
| *Bordetella pertussis* | 11 |
| *Chlamydophila pneumoniae* | 15 |
| *Haemophilus influenzae* | 20 |
| *Mycoplasma pneumoniae* | 10 |
| *Klebsiella pneumoniae* | 19 |
| *Legionella pneumophila* | 9 |
| *Moraxella catarrhalis* | 6 |
| *Pseudomonas aeruginosa* | 7 |
| *Staphylococcus aureus* | 17 |
| *Streptococcus pneumoniae* | 5 |
| Total | 119 |

The sequences of the 16S rRNA gene derived from 119 strains of the bacterial species were compared. As a result, 4 candidate primers were selected.

TABLE 2

| Name | Strand | Sequence (SEQ ID NO.) | Number of Ambiguous Nucleotides | Length (bp) | Mean Tm (□) |
| --- | --- | --- | --- | --- | --- |
| P0321 | forward | 1 | 2 | 20 | 72 |
| P0521 | reverse | 2 | 2 | 22 | 75 |
| P0930 | Forward | 23 | 1 | 20 | 76 |
| P1055 | Reverse | 24 | 2 | 23 | 77 |
| P1391 | Forward | 25 | 2 | 18 | 67 |
| P1499 | reverse | 26 | 2 | 21 | 66 |

It has been found that 10 of the candidate primer sets shown in Table 2 containing the oligonucleotides of SEQ ID NO:1 AND SEQ ID NO:2 can most efficiently amplify the 16S rRNA gene derived from the 10 bacterial species.

The present invention provides at least one probe oligonucleotide or probe oligonucleotide set specific for target nucleic acids of at least one bacteria selected from the group consisting of *Bordetella pertussis, Chlamydophila pneumoniae, Haemophilus influenzae, Klebsiella pneumoniae, Legionella pneumophila, Moraxella catarrhalis, Mycoplasma pneumoniae, Pseudomonas aeruginosa, Stapylococcus aureus*, and *Streptococcus pneumoniae*, comprising at least one oligonucleotide selected from the group consisting of:

at least one oligonucleotide of 10 to 100 nucleotides in length, selected from the group consisting of oligonucleotides comprising a fragment of at least 10 contiguous nucleotides present in sequences as set forth in SEQ ID NOS: 3 and 4 and their complementary sequences, which is specifically hybridizable with a nucleic acid derived from *Bordetella pertussis;* at least one oligonucleotide of 10 to 100 nucleotides in length, selected from the group consisting of oligonucleotides comprising a fragment of at least 10 contiguous nucleotides present in sequences as set forth in SEQ ID NOS: 5 and 6 and their complementary sequences, which is specifically hybridizable with a nucleic acid derived from *Chlamydophila pneumoniae;* at least one oligonucleotide of 10 to 100 nucleotides in length, selected from the group consisting of oligonucleotides comprising a fragment of at least 10 contiguous nucleotides present in sequences as set forth in SEQ ID NOS: 7 and 8 and their complementary sequences, which is specifically hybridizable with a nucleic acid derived from *Haemophilus influenzae;* at least one oligonucleotide of 10 to 100 nucleotides in length, selected from the group consisting of oligonucleotides comprising a fragment of at least 10 contiguous nucleotides present in sequences as set forth in SEQ ID NOS: 9 and 10 and their complementary sequences, which is specifically hybridizable with a nucleic acid derived from *Klebsiella pneumoniae;* at least one oligonucleotide of 10 to 100 nucleotides in length, selected from the group consisting of oligonucleotides comprising a fragment of at least 10 contiguous nucleotides present in sequences as set forth in SEQ ID NOS: 11 and 12 and their complementary sequences, which is specifically hybridizable with a nucleic acid derived from *Legionella pneumophila;* at least one oligonucleotide of 10 to 100 nucleotides in length, selected from the group consisting of oligonucleotides comprising a fragment of at least 10 contiguous nucleotides present in sequences as set forth in SEQ ID NOS: 13 and 14 and their complementary sequences, which is specifically hybridizable with a nucleic acid derived from *Moraxella catarrhalis;* at least one oligonucleotide of 10 to 100 nucleotides in length, selected from the group consisting of oligonucleotides comprising a fragment of at least 10 contiguous nucleotides present in sequences as set forth in SEQ ID NOS: 15 and 16 and their complementary sequences, which is specifically hybridizable with a nucleic acid derived from *Mycoplasma pneumoniae;* at least one oligonucleotide of 10 to 100 nucleotides in length, selected from the group consisting of oligonucleotides comprising a fragment of at least 10 contiguous nucleotides present in sequences as set forth in SEQ ID NOS: 17 and 18 and their complementary sequences, which is specifically hybridizable with a nucleic acid derived from *Pseudomonas aeruginosa;* at least one oligonucleotide of 10 to 100 nucleotides in length, selected from the group consisting of oligonucleotides comprising a fragment of at least 10 contiguous nucleotides present in sequences as set forth in SEQ ID NOS: 19 and 20 and their complementary sequences, which is specifically hybridizable with a nucleic acid derived from *Staphylococcus aureus;* and at least one oligonucleotide of 10 to 100 nucleotides in length, selected from the group consisting of oligonucleotides comprising a fragment of at least 10 contiguous nucleotides present in sequences as set forth in SEQ ID NOS: 21 and 22 and their complementary sequences, which is specifically hybridizable with a nucleic acid derived from *Streptococcus pneumoniae*. The probe oligonucleotides of the present invention can be used as a probe for specifically detecting a specific species within the 10 bacterial species.

In the present invention, "probe" means a hybridization probe and an oligonucleotide capable of sequence-specifically binding to a complementary strand of a nucleic acid. In the present invention, an oligonucleotide may be peptide nucleic acid, DNA, or RNA. The oligonucleotides of the present invention can be used in any method in which a specific species is to be detected among the 10 bacterial species. For example, the oligonucleotides of the present invention can be used in methods using a solid substrate on which the oligonucleotides are immobilized.

The probes of the present invention can specifically detect nucleic acids amplified through PCR using the genomes of the 10 bacterial species related to respiratory disease as a template and at least one oligonucleotide of 10 to 100 nucleotides in length, selected from the group consisting of oligonucleotides each of which comprises a fragment of at least 10 contiguous nucleotides present in a sequence as set forth in SEQ ID NO: 1 and at least one oligonucleotides of 10 to 100 nucleotides in length, selected from the group consisting of oligonucleotides each of which comprises a fragment of at least 10 contiguous nucleotides present in a sequence as set forth in SEQ ID NO: 2 as primers. The probes binding regions are as shown in Table 3.

TABLE 3

| Probe Name | SEQ ID NO. | Start position of binding to Amplicon | End position of binding to Amplicon | Detection |
| --- | --- | --- | --- | --- |
| BP-F2-2 | 3 | 126 | 148 | Antisense |
| BP-R2-3 | 4 | 85 | 112 | Sense |
| CP-F2-4 | 5 | 125 | 150 | Antisense |
| CP-F2-4 | 6 | 161 | 187 | Antisense |
| HI-F2-4 | 7 | 120 | 145 | Antisense |
| HI-R2-1 | 8 | 88 | 115 | Sense |
| KP-F2-4 | 9 | 135 | 161 | Antisense |
| KP-F2-5 | 10 | 159 | 182 | Antisense |
| LP-F1-1 | 11 | 144 | 169 | Antisense |
| LP-R2-4 | 12 | 109 | 131 | Sense |
| MC-F2-4 | 13 | 133 | 160 | Antisense |
| MC-F2-4 | 14 | 151 | 177 | Antisense |
| MP-F1-4 | 15 | 165 | 192 | Antisense |
| MP-R2-2 | 16 | 124 | 145 | Sense |
| PA-F1-1 | 17 | 141 | 164 | Antisense |
| PA-F2-3 | 18 | 156 | 182 | Antisense |
| SA-F1-2 | 19 | 139 | 164 | Antisense |
| SA-F2-4 | 20 | 172 | 198 | Antisense |
| SP-F2-3 | 21 | 143 | 169 | Antisense |
| SP-R2-4 | 22 | 112 | 136 | Sense |

The primer set and the oligonucleotide probes of the present invention can be used in a method of detecting the presence of particular bacteria. The method can comprise carrying out PCR using the primer set as a primer and nucleic acids isolated from a sample containing one or more species of the 10 bacterial species as a template, and then detecting the obtained PCR product by allowing the oligonucleotide probes capable of specifically binding to each of the bacterial species to react therewith. In this case, the oligonucleotide probes may be labeled with a proper marker generating a detectable signal.

Accordingly, the present invention provides a method of detecting the presence of one or more bacteria from the group consisting of *Bordetella pertussis, Chlamydophila pneumoniae, Haemophilus influenzae, Klebsiella pneumoniae,*

*Legionella pneumophila, Moraxella catarrhalis, Mycoplasma pneumoniae, Pseudomonas aeruginosa, Stapylococcus aureus,* and *Streptococcus pneumoniae*. The method comprises carrying out PCR using nucleic acids isolated from a sample containing the bacteria as a template and a primer set comprising the at least one oligonucleotide of 10 to 100 nucleotides in length, selected from the group consisting of oligonucleotides each of which comprises a fragment of at least 10 contiguous nucleotides present in a sequence as set forth in SEQ ID NO: 1 and the at least one oligonucleotides of 10 to 100 nucleotides in length, selected from the group consisting of oligonucleotides each of which comprises a fragment of at least 10 contiguous nucleotides present in a sequence as set forth in SEQ ID NO: 2 as a primer, and detecting the obtained PCR product using at least probe oligonucleotide of 10 to 100 nucleotides in length, selected from the group consisting of oligonucleotides each of which comprises a fragment of at least 10 contiguous nucleotides present in sequences as set forth in SEQ ID NOS: 3-22 as probes.

In the method of the present invention, the term "a polymerase chain reaction (PCR)" refers to a method of amplifying a target nucleic acid from a primer pair which is specifically bound to the target nucleic acid using a polymerase. Such a PCR is well known in the art and can also use a commercially available kit. The PCR includes a single PCR which amplifies one target once and a multiple PCR which amplifies a plurality of targets once. The multiple PCR uses a plurality of primer pairs.

In the method of the present invention, the detection of at least one bacteria may be accomplished by labeling the PCR product with a material generating a detectable signal, hybridizing the labeled PCR product with the probe oligonucleotide, and detecting the generated signal. The detectable signal may be an optical signal or an electrical signal, but is not limited thereto. The optically active material may be a fluorescent or phosphorescent material. The fluorescent material may be fluorescein, Cy-5, and Cy-3. Also, the PCR product may or may not be labeled with the material generating a detectable signal before or after hybridization. The hybridization of the PCR product which is not labeled with the probe oligonucleotide may be detected through an electrical signal, but other methods can also be used.

The present invention also provides a microarray having a substrate on which the probe oligonucleotide or the probe oligonucleotide set of the present invention is immobilized.

In the microarray of the present invention, the term "a microarray" refers to a substrate on which polynucleotide molecules are immobilized at fixed locations. Such a microarray is well known in the art and examples thereof can be found in, for example, U.S. Pat. Nos. 5,445,934 and 5,744,305, the disclosures of which are incorporated herein in their entirety by reference. The probe oligonucleotide or the probe oligonucleotide set are as described above.

Hereinafter, the present invention will be described in detail with reference to the following Example. However, the scope of the present invention is not limited by this example.

EXAMPLE 1

Detection of Target Bacteria Using Microarray on which Probes Specific to 9 Bacteria Species Related to Respiratory Diseases are Immobilized A microarray in which two oligonucleotides (respectively, SEQ ID NO:3 and SEQ ID NO:4, SEQ ID NO:7 and SEQ ID NO:8; SEQ ID NO:9 and SEQ ID NO:10; SEQ ID NO:11 and SEQ ID NO:12; SEQ ID NO:13 and SEQ ID NO:14; SEQ ID NO:15 and SEQ ID NO:16; SEQ ID NO:17 and SEQ ID NO:18; SEQ ID NO:19 and SEQ ID NO:20; or SEQ ID NO:21 and SEQ ID NO:22) specific to respective nucleic acids derived from *Bordetella pertussis, Haemophilus influenzae, Klebsiella pneumoniae, Legionella pneumophila, Moraxella catarrhalis, Mycoplasma pneumoniae, Pseudomonas aeruginosa, Stapylococcus aureus,* and *Streptococcus pneumoniae* were immobilized on 4 spot regions, respectively, was prepared. The presence of target bacteria in a sample was then identified using the prepared microarray.

Figure 1:
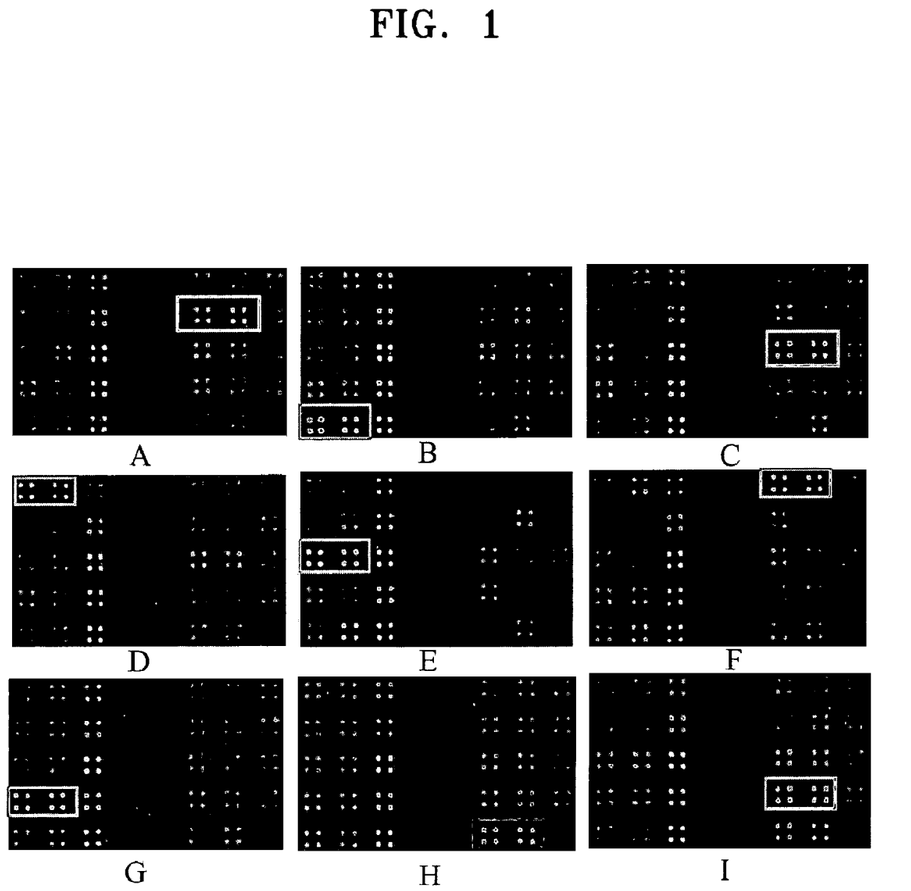
FIG. 1 shows the results of hybridization on a microarray according to the present invention expressed by fluorescent intensity at 540 nm.

To prepare the microarray, the species-specific oligonucleotides were placed on the substrate activated with amine compounds and then allowed to react at 50° C. for 30 minutes to immobilize on the substrate. A sample containing nucleic acids derived from each of the 9 bacterial species described above was placed on the spots of the obtained microarray and a hybridization reaction was carried out at 16° C. for 12 hours. FIG. 1 shows the results of hybridization on the microarray expressed by fluorescent intensity at 540 nm. As shown in FIG. 1, it was confirmed that each of the oligonucleotides of the present invention could be used as probes specific to all of the species. In FIG. 1, A, B, C, D, E, F, G, H, and I show the results of hybridization on a microarray with the oligonucleotides specific to *Bordetella pertussis, Haemophilus influenzae, Mycoplasma pneumoniae, Klebsiella pneumoniae, Legionella pneumophila, Moraxella catarrhalis, Pseudomonas aeruginosa, Staphylococcus aureus, Streptococcus pneumoniae*, respectively, immobilized thereon (Refer to square parts).

Conventionally, no single primer set capable of detecting the 10 bacterial species related to respiratory diseases are known. However, the primer set of the present invention can be used to amplify in common a target sequence found in 11 strains of *Bordetella pertussis*, 15 strains of *Chlamydophila pneumoniae*, 20 strains of *Haemophilus influenzae*, 10 strains of *Mycoplasma pneumoniae*, 19 strains of *Klebsiella pneumoniae*, 9 strains of *Legionella pneumophila*, 6 strains of *Moraxella catarrhalis*, 7 strains of *Pseudomonas aeruginosa*, 17 strains of *Stapylococcus aureus*, and 5 strains of *Streptococcus pneumoniae*, that is, 119 strains of the 10 bacterial species.

The primer set of the present invention can be used to amplify a target sequence in the 10 bacterial species related to respiratory diseases without the use of other primers.

The probes of the present invention can be used to detect a specific species without a cross reaction with the nucleic acid found in the 10 bacterial species related to respiratory diseases occurring.

According to a method of the present invention, at east one bacteria selected from the group consisting of 10 bacterial species related to respiratory diseases can be efficiently detected.

A microarray of the present invention is useful for detection of at east one bacteria selected from the group consisting of 10 bacterial species related to respiratory diseases.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of detecting the presence of one or more bacteria selected from the group consisting of *Bordetella pertussis, Chlamydophila pneumoniae, Haemophilus influenzae, Klebsiella pneumoniae, Legionella pneumophila, Moraxella catarrhalis, Mycoplasma pneumoniae, Pseudomonas aeruginosa, Staphylococcus aureus*, and *Streptococcus pneumoniae*, the method comprising:

carrying out PCR using nucleic acids isolated from a sample containing bacteria as a template and a primer set as a primer, the primer set for amplifying a target sequence specific to *Bordetella pertussis, Chlamydophila pneumoniae, Haemophilus influenzae, Klebsiella pneumoniae, Legionella pneumophila, Moraxella catarrhalis, Mycoplasma pneumoniae, Pseudomonas aeruginosa, Staphylococcus aureus*, and *Streptococcus pneumoniae*, the primer set comprising an oligonucleotide consisting of SEQ ID NO: 1 and an oligonucleotide consisting of SEQ ID NO: 2; and detecting the obtained PCR product using a probe oligonucleotide set as probes, wherein the probe oligonucleotide set is specific for target nucleic acids of bacteria consisting of *Bordetella pertussis, Chlamydophila pneumoniae, Haemophilus influenzae, Klebsiella pneumoniae, Legionella pneumophila, Moraxella catarrhalis, Mycoplasma pneumoniae, Pseudomonas aeruginosa, Staphylococcus aureus*, and *Streptococcus pneumoniae*, the probe oligonucleotide set comprising:

oligonucleotides of SEQ ID NOS: 3 and 4, which are specifically hybridizable with a nucleic acid from *Bordetella pertussis* and which do not cross-hybridize with a nucleic acid from *Chlamydophila pneumoniae, Haemophilus influenzae, Klebsiella pneumoniae, Legionella pneumophila, Moraxella catarrhalis, Mycoplasma pneumoniae, Pseudomonas aeruginosa, Staphylococcus aureus*, and *Streptococcus pneumoniae*.

2. The method of claim 1, wherein the probe oligonucleotide set further comprises:

oligonucleotides of SEQ ID NOS: 5 and 6, which are specifically hybridizable with a nucleic acid from *Chlamydophila pneumoniae;* oligonucleotides of SEQ ID NOS: 7 and 8, which are specifically hybridizable with a nucleic acid from *Haemophilus influenzae;* oligonucleotides of SEQ ID NOS: 9 and 10, which are specifically hybridizable with a nucleic acid from *Klebsiella pneumoniae;* oligonucleotides of SEQ ID NOS: 11 and 12, which are specifically hybridizable with a nucleic acid from *Legionella pneumophila;* oligonucleotides of SEQ ID NOS: 13 and 14, which are specifically hybridizable with a nucleic acid from *Moraxella catarrhalis;* oligonucleotides of SEQ ID NOS: 15 and 16, which are specifically hybridizable with a nucleic acid from *Mycoplasma pneumoniae;* oligonucleotides of SEQ ID NOS: 17 and 18, which are specifically hybridizable with a nucleic acid from *Pseudomonas aeruginosa;* oligonucleotides of SEQ ID NOS: 19 and 20, which are specifically hybridizable with a nucleic acid from *Staphylococcus aureus*; and oligonucleotides of SEQ ID NOS: 21 and 22, which are specifically hybridizable with a nucleic acid from *Streptococcus pneumoniae*, and the probe oligonucleotide set is immobilized on a microarray substrate.

3. A microarray having a substrate on which a probe oligonucleotide set is immobilized, wherein the probe oligonucleotide set is specific for target nucleic acids of bacteria consisting of *Bordetella pertussis, Chlamydophila pneumoniae, Haemophilus influenzae, Klebsiella pneumoniae, Legionella pneumophila, Moraxella catarrhalis, Mycoplasma pneumoniae, Pseudomonas aeruginosa, Staphylococcus aureus*, and *Streptococcus pneumoniae*, the probe oligonucleotide set comprising:

oligonucleotides of SEQ ID NOS: 3 and 4, which are specifically hybridizable with a nucleic acid from *Bordetella pertussis* and which do not cross-hybridize with a nucleic acid from *Chlamydophila pneumoniae, Haemophilus influenzae, Klebsiella pneumoniae, Legionella pneumophila, Moraxella catarrhalis, Mycoplasma pneumoniae, Pseudomonas aeruginosa, Staphylococcus aureus*, and *Streptococcus pneumoniae*.

4. The microarray of claim 3, wherein the probe oligonucleotide set further comprises:

oligonucleotides of SEQ ID NOS: 5 and 6, which are specifically hybridizable with a nucleic acid from *Chlamydophila pneumoniae;* oligonucleotides of SEQ ID NOS: 7 and 8, which are specifically hybridizable with a nucleic acid from *Haemophilus influenzae;* oligonucleotides of SEQ ID NOS: 9 and 10, which are specifically hybridizable with a nucleic acid from *Klebsiella pneumoniae;* oligonucleotides of SEQ ID NOS: 11 and 12, which are specifically hybridizable with a nucleic acid from *Legionella pneumophila;* oligonucleotides of SEQ ID NOS: 13 and 14, which are specifically hybridizable with a nucleic acid from *Moraxella catarrhalis;* oligonucleotides of SEQ ID NOS: 15 and 16, which are specifically hybridizable with a nucleic acid from *Mycoplasma pneumoniae;* oligonucleotides of SEQ ID NOS: 17 and 18, which are specifically hybridizable with a nucleic acid from *Pseudomonas aeruginosa;* oligonucleotides of SEQ ID NOS: 19 and 20, which are specifically hybridizable with a nucleic acid from *Staphylococcus aureus;* and oligonucleotides of SEQ ID NOS: 21 and 22, which are specifically hybridizable with a nucleic acid from *Streptococcus pneumoniae*.

* * * * *

SEQUENCE LISTING

<160> NUMBER OF SEQ ID NOS: 26

<210> SEQ ID NO 1
<211> LENGTH: 19
<212> TYPE: DNA
<213> ORGANISM: Artificial sequence
<220> FEATURE:
<223> OTHER INFORMATION: forward primer

<400> SEQUENCE: 1
ccakactcct acgggaggc                                                      19

<210> SEQ ID NO 2
<211> LENGTH: 22
<212> TYPE: DNA
<213> ORGANISM: Artificial sequence
<220> FEATURE:
<223> OTHER INFORMATION: reverse primer

<400> SEQUENCE: 2
gtgccagcag yygcggtaat ac                                                  22

<210> SEQ ID NO 3
<211> LENGTH: 21
<212> TYPE: DNA
<213> ORGANISM: Artificial sequence
<220> FEATURE:
<223> OTHER INFORMATION: B.pertussis probe

<400> SEQUENCE: 3
ttggcaggaa agaaacggca c                                                   21

<210> SEQ ID NO 4
<211> LENGTH: 26
<212> TYPE: DNA
<213> ORGANISM: Artificial sequence
<220> FEATURE:
<223> OTHER INFORMATION: B. pertussis probe

<400> SEQUENCE: 4
tctttcctgc caaagtgct ttacaa                                               26

<210> SEQ ID NO 5
<211> LENGTH: 24
<212> TYPE: DNA
<213> ORGANISM: Artificial sequence
<220> FEATURE:
<223> OTHER INFORMATION: C. pneumoniae specific probe

<400> SEQUENCE: 5
ttcgcctggg aataagagag rttg                                                24

<210> SEQ ID NO 6
<211> LENGTH: 25
<212> TYPE: DNA
<213> ORGANISM: Artificial sequence
<220> FEATURE:
<223> OTHER INFORMATION: C. pneumoniae specific probe

<400> SEQUENCE: 6
tygatttgag cgtaccrggt aaaga                                               25

<210> SEQ ID NO 7
<211> LENGTH: 24

```
<212> TYPE: DNA
<213> ORGANISM: Artificial Sequence
<220> FEATURE:
<223> OTHER INFORMATION: H.influenzae specific probe

<400> SEQUENCE: 7
gttctttcgg tattgaggaa ggkw                                    24

<210> SEQ ID NO 8
<211> LENGTH: 26
<212> TYPE: DNA
<213> ORGANISM: Artificial sequence
<220> FEATURE:
<223> OTHER INFORMATION: H.influenzae specific probe

<400> SEQUENCE: 8
tcaataccga aagaacttta caaccc                                  26

<210> SEQ ID NO 9
<211> LENGTH: 25
<212> TYPE: DNA
<213> ORGANISM: Artificial sequence
<220> FEATURE:
<223> OTHER INFORMATION: K. pneumoniae specific probe

<400> SEQUENCE: 9
aggaaggcgd traggttaat aacct                                   25

<210> SEQ ID NO 10
<211> LENGTH: 22
<212> TYPE: DNA
<213> ORGANISM: Artificial sequence
<220> FEATURE:
<223> OTHER INFORMATION: K.pneumoniae specific probe

<400> SEQUENCE: 10
tyrtcgattg acgttacccg ca                                      22

<210> SEQ ID NO 11
<211> LENGTH: 25
<212> TYPE: DNA
<213> ORGANISM: Artificial sequence
<220> FEATURE:
<223> OTHER INFORMATION: L. pneumoniae specific probe

<400> SEQUENCE: 11
tgataggtta agagctratt aactg                                   25

<210> SEQ ID NO 12
<211> LENGTH: 21
<212> TYPE: DNA
<213> ORGANISM: Artificial sequence
<220> FEATURE:
<223> OTHER INFORMATION: L. pneumoniae specific probe

<400> SEQUENCE: 12
aaccctcagg ccttcttcac a                                       21

<210> SEQ ID NO 13
<211> LENGTH: 26
<212> TYPE: DNA
<213> ORGANISM: Artificial sequence
<220> FEATURE:
<223> OTHER INFORMATION: M. catarrhalis specific probe

<400> SEQUENCE: 13
```

-continued ggaggaaaag cttatggtta ataccc                                          26

<210> SEQ ID NO 14
<211> LENGTH: 25
<212> TYPE: DNA
<213> ORGANISM: Artificial sequence
<220> FEATURE:
<223> OTHER INFORMATION: M. catarrhalis specific probe

<400> SEQUENCE: 14
taatacccat aagccctgac gttac                                           25

<210> SEQ ID NO 15
<211> LENGTH: 27
<212> TYPE: DNA
<213> ORGANISM: Artificial sequence
<220> FEATURE:
<223> OTHER INFORMATION: M. pneumoniae specific probe

<400> SEQUENCE: 15
agtttgactg taccattttg aataagt                                         27

<210> SEQ ID NO 16
<211> LENGTH: 20
<212> TYPE: DNA
<213> ORGANISM: Artificial sequence
<220> FEATURE:
<223> OTHER INFORMATION: M. pneumoniae specific probe

<400> SEQUENCE: 16
tcatcgttca cgcggcattg                                                 20

<210> SEQ ID NO 17
<211> LENGTH: 23
<212> TYPE: DNA
<213> ORGANISM: Artificial sequence
<220> FEATURE:
<223> OTHER INFORMATION: P.aeruginosa specific probe

<400> SEQUENCE: 17
gggcagtaag ttaatacctt gct                                             23

<210> SEQ ID NO 18
<211> LENGTH: 25
<212> TYPE: DNA
<213> ORGANISM: Artificial sequence
<220> FEATURE:
<223> OTHER INFORMATION: P.aeruginosa specific probe

<400> SEQUENCE: 18
ccttgctgtt ttgacgttac caaca                                           25

<210> SEQ ID NO 19
<211> LENGTH: 25
<212> TYPE: DNA
<213> ORGANISM: Artificial sequence
<220> FEATURE:
<223> OTHER INFORMATION: S.aureus specific probe

<400> SEQUENCE: 19
aacatatgtg taagtaactg tgcac                                           25

<210> SEQ ID NO 20
<211> LENGTH: 25
<212> TYPE: DNA
<213> ORGANISM: Artificial sequence

```
<220> FEATURE:
<223> OTHER INFORMATION: S.aureus specific probe

<400> SEQUENCE: 20
gtacctaatc agaaagccac ggcta                                          25

<210> SEQ ID NO 21
<211> LENGTH: 25
<212> TYPE: DNA
<213> ORGANISM: Artificial sequence
<220> FEATURE:
<223> OTHER INFORMATION: S. pneumoniae specific probe

<400> SEQUENCE: 21
gtgtgagagt ggaaagttca cactg                                          25

<210> SEQ ID NO 22
<211> LENGTH: 23
<212> TYPE: DNA
<213> ORGANISM: Artificial sequence
<220> FEATURE:
<223> OTHER INFORMATION: S. pneumoniae specific probe

<400> SEQUENCE: 22
tccgaaaacc ttcttcactc acg                                            23

<210> SEQ ID NO 23
<211> LENGTH: 20
<212> TYPE: DNA
<213> ORGANISM: Artificial sequence
<220> FEATURE:
<223> OTHER INFORMATION: forward primer

<400> SEQUENCE: 23
aattgacggg grcccgcaca                                                20

<210> SEQ ID NO 24
<211> LENGTH: 23
<212> TYPE: DNA
<213> ORGANISM: Artificial sequence
<220> FEATURE:
<223> OTHER INFORMATION: reverse primer

<400> SEQUENCE: 24
ctgacgacar ccatgcasca cct                                            23

<210> SEQ ID NO 25
<211> LENGTH: 18
<212> TYPE: DNA
<213> ORGANISM: Artificial sequence
<220> FEATURE:
<223> OTHER INFORMATION: forward primer

<400> SEQUENCE: 25
gtgaatacgt tcycgggy                                                  18

<210> SEQ ID NO 26
<211> LENGTH: 21
<212> TYPE: DNA
<213> ORGANISM: Artificial sequence
<220> FEATURE:
<223> OTHER INFORMATION: reverse primer

<400> SEQUENCE: 26
ggbtaccttg ttacgacttm a                                              21
```